United States Patent [19]
Fitzgerald

[11] Patent Number: 5,932,564
[45] Date of Patent: Aug. 3, 1999

[54] METHODS FOR THE PREVENTION AND TREATMENT OF GASTROINTESTINAL DISORDERS

[75] Inventor: Jamesina Anne Fitzgerald, Hamilton, Ohio

[73] Assignee: The Procter & Gamble Company, Cincinnati, Ohio

[21] Appl. No.: 08/780,526

[22] Filed: Jan. 8, 1997

Related U.S. Application Data

[63] Continuation of application No. 08/568,853, Dec. 7, 1995, abandoned.

[51] Int. Cl.$^6$ ............................ A61K 31/60; A61K 31/29
[52] U.S. Cl. ............................................ 514/159; 514/503
[58] Field of Search ...................................... 514/159, 503

[56] References Cited

U.S. PATENT DOCUMENTS

| | | | |
|---|---|---|---|
| 4,049,817 | 9/1977 | Laber et al. | 424/270 |
| 4,514,421 | 4/1985 | Herschler | 514/711 |
| 5,221,664 | 6/1993 | Berkowitz et al. | 514/6 |
| 5,256,684 | 10/1993 | Marshall | 514/398 |

FOREIGN PATENT DOCUMENTS

| | | | |
|---|---|---|---|
| 0962163 | 6/1950 | France . | |
| 63-174926 | 7/1988 | Japan | A61K 31/29 |
| WO 92/01457 | 2/1992 | WIPO | A61K 33/24 |

OTHER PUBLICATIONS

Derwent Abstract of Wolfe, "Acute Diarrhea Associated with Travel", Am. J. Med 88(6A) pp. 34S–37S, 1990.

Cavier, R., "Etude des propriérés parasiticides de quelques complexes bismuthiques de l'oxy–8 quinoléine", Annales pharmaceutiques francaises, 1973, 31, No. 4, pp. 173–178 (translation attached).

Pitlik, S., et al., "Cryptosporidial Cholecystitis", The New England Journal of Medicine, vol. 308, No. 16 (Apr. 21, 1983), p. 967.

Than, et al., "The Alkaloids of Holarrhena Antidysenterica", Union of Burma Journal of Science and Technology, pp. 423–436 (Dec. 1969).

Willard, et al., "Survey of Chemical Compounds Tested in Vitro Against Rumen Protozoa for Possible Control of Bloat", Applied Microbiology, pp. 1014–1019 (Sep. 1967).

Chevalier, C., et al., "Bilan Des Antiparasitaires A Usage Veterinaire: Antihelminthiques, Anticoccidiens, Antifongiques, Ecotparasiticides" (translation attached), Laboratory of Therapeutic Chemistry, College of Pharmacy , 37042 Tours Cedex, pp. 624–630.

DuPont, H., et al., Symptomatic Treatment of Diarrhea With Bismuth Subsalicylate Among Students Attending a Mexican University, Gastoenterology, vol. 73, (1977), pp. 715–718.

DuPont, H., "Enteropathogenic Organisms: New Etiologic Agents and Concepts of Disease", Medical Clinics of North America, vol. 62, No. 5 (1978), pp. 945–960.

Wolfe, M., "The Treatment of Intestinal Protozoan Infections", Medical Clinics of North America, vol. 56, No. 3 (1982), pp. 707–720.

Journal of the American Medical Association, "Travelers' Diarrhea", vol. 253, No. 18 (1985), pp. 2700–2704.

DuPont, L., "Nonfluid Therapy and Selected Chemoprophylaxis of Acute Diarrhea", The American Journal of Medicine, vol. 78, Suppl. 6B (1985), pp. 81–90.

Johnson, P., et al., "Comparison of Loperamide With Bismuth Subsalicylate for the Treatment of Acute Traveler's Diarrhea", The Journal Of the American Medical Association, vol. 255, No. 6 (1986), pp. 757–760.

Steffen, R., "Anerkannte Prinzipien zur Prophylaxe und Therapie der Reisediarrhoe", Schweiz. med. Wschr. 116, Nr. 20 (1986), pp. 670–673 (translation provided).

DuPont, H., et al., "Prevention of Travelers' Diarrhea By the Tablet Formulation of Bismuth Subsalicylate", The Journal of the American Medical Association, vol. 257, No. 10 (1987), pp. 1347–1350.

White, N., "Drug Treatment and Prevention of Malaria", European Journal of Clinical Pharmacology, vol. 34 (1988), pp. 1–14.

D'Alessandro, A., "Amebiasis Then", American Journal of Tropical Medicine and Hygiene, vol. 41, No. 3, Suppl. (1989), pp. 38–39.

Steffen, R., "Worldwide Efficacy of Bismuth Subsalicylate in the Treatment of Travelers' Diarrhea", Reviews of Infections Diseases, vol. 12, Suppl. 1 (1990), pp. S80–S86.

Long, E., et al., "Alga Associated with Diarrhea in Patients with Acquired Immunodeficiency Syndrome and in Travelers", Journal of Clinical Microbiology, vol. 28, No. 6 (1990), pp. 1101–1104.

Wolfe, M., "Acute Diarrhea Associated With Travel", The American Journal of Medicine, vol. 88, Suppl. 6A (1990), pp. 34S–37S.

Qadri, S.M.H., "Infectious Diarrhea: Managing a Misery that is Still Worldwide", Postgraduate Medicine, vol. 88, No. 5 (1990), pp. 169–184).

Farthing, M.J.G., et al., "Treatment and Prevention of Travellers' Diarrhoea", Gastroenterology International, vol. 5, No. 3 (1992), pp. 162–175.

Zinsser Microbiology, 20th ed., Appleton & Lange (1992), pp. 1161–1173.

Arduino, R., et al., "Travellers' Diarrhoea", Bailliere's Clinical Gastroenterology, vol. 7, No. 2 (1993), pp. 365–385.

Chak, A., et al., "Traveler's Diarrhea", Gastroenterology Clinics of North America, vol. 22, No. 3 (1993), pp. 549–561.

(List continued on next page.)

*Primary Examiner*—Raymond Henley, III
*Attorney, Agent, or Firm*—Kirsten K. Stone; Mary Catherine Hentz

[57] ABSTRACT

The subject invention encompasses methods for the prevention and treatment of a human or lower animal subject having a gastrointestinal disorder caused or mediated by one or more intestinal helminths comprising administering bismuth to the subject.

6 Claims, No Drawings

OTHER PUBLICATIONS

American Health Consultants, "Cryptosporidiosis in Milwaukee", vol. 12, No. 15 (1993), pp. 113–115.

Wittner, M., et al., "Parasitic Infections in AIDS Patients: Cryptosporidiosis, Isosporiasis, Microsporidiosis, Cyclosporiasis", Infectious Disease Clinics of North America, vol. 7, No. 3 (1993), pp. 569–586.

Weber, R., et al., "Disseminated Microsporidiosis Due to *Encephalitozoon Hellem:* Pulmonary Colonization, Microhematuria, and Mild Conjuctivitis in a Patient with AIDS", Clinical Infectious Diseases, vol. 17 (1993), pp. 415–419.

Kuhls, T., "Protozoal Infections of the Intestinal Tract in Children", Advances in Pediatric Diseases, vol. 8 (1993), pp. 177–202.

Scott, D., et al., "Treatment of Gastrointestinal Infections", Bailliere's Clinical Gastroenterology, vol. 7, No. 2 (1993), pp. 477–499.

Martindale, The Extra Pharmacopoeia, "Gastro–intestinal Agents", Thirtieth Ed., The Pharmaceutical Press (1993), p. 872.

Health, "Are Milwaukee–Type Parasites Floating in My Drinking Water ?" (1993), p. 14.

Sun, T., et al., "Intestinal Microsporidiosis: Report of Five Cases", Annals of Clinical and Laboratory Science, vol. 24, No. 6 (1994), pp. 521–532.

American Drug Index, 38th Ed. (1994), pp. 568–569.

Upcroft, P., "Multiple Drug Resistance in the Pathogenic Protozoa", Acta Tropica, vol. 56 (1994), pp. 195–212.

Herwaldt, B., et al., "Infections with Intestinal Parasites in Peace Corps Volunteers in Guatemala", Journal of Clinical Microbiology (1994), pp. 1376–1378.

Physicians' Desk Reference, 48th Ed. (1994), pp. 724–726.

Jernigan, et al., "Parasitic Infections of the Small Intestine", Gut, vol. 35, No. 3 (1994), pp. 289–293.

Fritsche, T., et al., "Introduction to Diagnostic Parasitology: Biologic, Clinical, and Laboratory Considerations", Manual of Clinical Microbiology, Sixth Ed., ASM Press (1995), pp. 1141–1144.

METHODS FOR THE PREVENTION AND TREATMENT OF GASTROINTESTINAL DISORDERS

This is a continuation of application Ser. No. 08/568,853, filed on Dec. 7, 1995 now abandoned.

BACKGROUND OF THE INVENTION

While many industrialized countries have come to regard infection by intestinal helminths as a problem of impoverished developing countries, this is far from true. The incidence of gastrointestinal infection by parasitic intestinal helminths continues to present a serious health concern. The World Health Organization and other authorities estimate that well over two billion of the population are infected annually with intestinal helminths. *Manual Of Clinical Microbiology*, Sixth Edition, 1141–1142. Worldwide, five hundred to eight hundred million are estimated to be infected with *Trichuris trichiura,* and nine hundred million with hookworm. Id. Treatment of helminth infections has had modest success due to the complexity of the parasitic life cycles of the organisms i.e., egg, first-stage larva, second-stage larva, third-stage larva, free-form, etc. In addition, an increasing display of resistance to commonly used antihelminthic agents further hinders the likelihood of successful treatment of helminth infections. Therefore, the need for effective antihelminthic therapies continues to grow.

It has been discovered by the present invention that the administration of bismuth salts may be effective for the prevention and/or treatment of gastrointestinal disorders caused or mediated by one or more intestinal helminths. Thus, an object of the present invention is to provide a safe and effective method of preventing and/or treating gastrointestinal disorders caused or mediated by intestinal helminths. A further object of the invention is to provide such a method comprising the administration of bismuth.

These and other objects of the present invention will become readily apparent from the detailed description which follows.

SUMMARY OF THE INVENTION

The present invention relates to a method for treatment of a human or lower animal subject having a gastrointestinal disorder caused or mediated by one or more intestinal helminths comprising administering to the subject from about 50 milligrams to about 5000 milligrams of bismuth, per day, for from about 1 to 56 days.

The present invention also relates to a method for prevention in a human or lower animal of a gastrointestinal disorder caused or mediated by one or more intestinal helminths comprising administering to the subject from about 50 milligrams to about 5000 milligrams of bismuth, per day, for from about 1 to 28 days.

DETAILED DESCRIPTION OF THE INVENTION

The methods of the present invention comprise the prevention and/or treatment of gastrointestinal disorder caused or mediated by one or more intestinal helminths. Such gastrointestinal disorders are prevented and/or treated by the administration of bismuth. The components of the present invention are more fully defined below.

Gastrointestinal Disorder

The term "gastrointestinal disorder", as used herein, encompasses any infection, disease or other disorder of body, typically of the upper and/or lower gastrointestinal tract, caused or mediated by one or more intestinal helminths. Such disorders include one or more of the following conditions: diarrhea, abdominal pain and/or cramping, epigastric fullness, constipation, blood and/or mucus present in feces, fever, vomiting, gastroenteritis, weight loss, anemia, malaise, pallor, anal pruritus, and any other condition commonly associated with infection by intestinal helminths. Severe infections may even result in dangerous migrations of infection to ectopic sites such as the liver, lungs, etc. or even death.

In immunocompromised subjects and children, gastrointestinal disorders caused or mediated by intestinal helminths may be more severe and life threatening than the common disorders listed above. Therefore, the term "gastrointestinal disorder" also includes any condition commonly associated with intestinal helminths in immunocompromised subjects and children, including but not limited to bloody diarrhea, extreme constipation, irritability, extreme pruritus, wasting, listlessness, bowel obstruction, and retardation of development.

Intestinal Helminths

Intestinal helminths, commonly referred to as worms, are multi-cellular parasites which have been implicated in intestinal disease. The term "intestinal helminths", as used herein, refers to helminths of the following medically important groups: Nematodes, Trematodes, and Cestodes. These organisms are fully described in *Zinsser Microbiology*, 20th Edition, 1195–1215, (1992) and *Manual of Clinical Microbiology*, Sixth Edition, 1141–1144, and 1229–1243, (1995), both of which are incorporated herein by reference.

Nematodes (or roundworms) include *Trichinella spiralis, Enterobius vermicularis* (pinworm), *Ascaris lumbricoides, Trichuris trichiura* (whipworm), *Capillaria philippinensis, Ancylcolostoma duodenale* (common hookworm), *Necator americanus* (American hookworm), and Trichostrongylus (species such as *Strongyloides stercoralis* (threadworm). Trematodes (fluke worms) include *Fasciolopsis buski, Heterophyes heterophyes, Metagoniumus yokogawai,* and *Nanophyetus salmincola.* Cestodes (or tapeworms) include *Diphyllobothrium latum, Taenia saginata, Taenia solium,* and *Hymenolepis nana.*

Preferred intestinal helminths are *Enterobius vermicularis, Ancylostoma duodenale, Trichuris trichiura, Fasciolopsis buski,* Trichostrongylus species, *Taenia saginata,* and combinations thereof. Most preferred parasitic protozoa are *Enterobius vermicularis, Ancylostoma duodenale, Trichuris trichiura,* and combinations thereof.

Diagnosis of gastrointestinal disorders caused or mediated by intestinal helminths may be accomplished by any method commonly used in the medical community. Such methods are fully described in *Zinsser Microbiology,* and *Manual of Clinical Microbiology,* as referenced above.

Bismuth

The methods of treatment and/or prevention in the present invention involve administration of bismuth. As used herein, the quantity of bismuth is by weight of elemental bismuth.

The preferred duration of bismuth administration will vary according to the specific gastrointestinal disorder to be treated and the physical condition of the subject being treated. In general, as a method of treatment, bismuth may be administered in an amount of from about 50 milligrams to about 5000 milligrams, and preferably from about 50 milligrams to about 2500 milligrams, per day, for from about 1 to about 56 days, preferably for from about 2 to about 28 days, and most preferably for from about 7 to about 21 days.

In general, as a method of prevention, bismuth may be administered in an amount of from about 50 milligrams to about 5000 milligrams, and preferably from about 50 milligrams to about 2500 milligrams, per day, for from about 1 to about 21 days, and preferably for from about 1 to about 14 days. In a method of prevention, bismuth may be administered prior to potential exposure to intestinal helminths. Such administration of bismuth may vary depending on the likelihood of intestinal helminth exposure and condition of the subject and may be commenced at any time deemed beneficial by the medical community including from about 1 to about 7 days, from about 2 to about 5 days, and from about 3 to about 4 days, prior to potential exposure.

In the present invention, the term "bismuth", as used herein, includes bismuth in the form of a pharmaceutically-acceptable salt, bismuth in the form of an organic or other complex which contains bismuth as an active ingredient, and mixtures thereof. Such organic complexes include 2,2'-spirobi[1,3,2-benzodoxabis-mole]. Preferably, bismuth is administered in the present methods as a pharmaceutically-acceptable salt. Such bismuth salts include bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention.

The bismuth useful herein may be administered alone, or in combination with other pharmaceutically-acceptable components in a bismuth-containing composition. A variety of such compositions containing bismuth salts are commercially available. Such compositions include DeNol, containing tripotassium dicitrato bismuthate (by Brocades); Bislumina, containing bismuth aluminate (by Mazuelos); Roter, containing bismuth subnitrate (by Roterpharma); Devrom®, containing bismuth subgallate (by The Parthenon Co., Inc.); and Pepto-Bismol®, containing bismuth subsalicylate (by The Procter & Gamble Company).

As used herein, the term "administering" refers to any method which, in sound medical practice delivers the compounds or compositions used in this invention to the subject to be treated in such a manner so as to be effective in the treatment of the gastrointestinal disorder. Preferably, the bismuth is administered orally.

The following non-limiting examples illustrate the methods and uses of the present invention.

EXAMPLE I

A South African farmer enters a health clinic in an extremely weakened condition with sallow skin and a tender abdomen, describing periods of alternating diarrhea and constipation. Fecal bacterial isolates fail to identify the offending pathogen. Direct wet mount examination of the fecal specimens reveals the presence of thin shelled eggs (40–60 μm) which confirms the diagnosis of *Ancylostoma duodenale*. Following the diagnosis, the patient is treated by administering a composition containing bismuth subsalicylate, sold by The Procter & Gamble Company under the name "Pepto-Bismol®". The composition, in liquid form, is administered four times daily in equal doses delivering approximately 2500 milligrams of bismuth per day, for 21 days. Thereafter, fecal samples from the subject are analyzed again, finding no trace of helminthic infection. The patient remains asymptomatic, and another fecal analysis performed 5 months later is normal.

In the above example, tripotassium dicitrate bismuthate tartrate, bismuth citrate, and bismuth subnitrate are substituted, respectively, for bismuth subsalicylate, with substantially similar results.

EXAMPLE II

A five-year-old child, from an indigent Appalachian family, is suffering from nausea, vomiting, and mucous diarrhea. Analysis of fecal specimens reveals the presence of barrel shaped eggs (20–50 μm in size, golden brown in color, and having a transparent prominence or polar plug at each end), characteristic of *Trichuris trichiura*. The infection is diagnosed and treated by orally administering approximately 400 milligrams of bismuth in the form of bismuth subcitrate ("DeNol" sold by Brocades), in four equal doses daily for about 28 days. Thereafter, fecal samples from the subject are analyzed again, finding no trace of helminthic infection.

EXAMPLE III

Eight children in a kindergarten class of twelve students have been diagnosed with pinworms. The parents of the four uninfected children solicit help from the student health service to prevent their children from becoming infected with *Enterobius vermicularis*. Clinical evaluation of the four children confirms that they had not been infected. The children are given approximately 800 milligrams of bismuth, in the form of bismuth subgalate (Devrom®, sold by The Parthenon Company, Inc.), in four equal doses daily for about 21 days. The four children remain asymptomatic. Fecal samples from all children of the kindergarten class are analyzed and no evidence of pinworm infection is found.

What is claimed is:

1. A method for reducing a population of one or more intestinal helminths selected from the group consisting of *Enterobius vermicularis, Ancylostoma duodenale, Trichuris trichiura, Fasciolopsis buski, Taenia saginata,* and combinations thereof, in a human or lower animal subject having a helminthic gastrointestinal disorder, consisting essentially of administering to the subject from about 50 milligrams to about 5000 milligrams of bismuth, per day, for from about 1 to 56 days.

2. The method of claim 1 wherein the bismuth is administered at a level of from about 50 milligrams to about 2500 milligrams, per day.

3. The method of claim 1 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

4. A method of preventing a helminthic infection caused or mediated by one or more intestinal helminths selected from the group consisting of *Enterobius vermicularis, Ancylostoma duodenale, Trichuris trichiura, Fasciolopsis buski, Taenia saginata,* and combinations thereof, in a human or lower animal subject consisting essentially of administering to the subject from about 50 milligrams to about 5000 milligrams of bismuth, per day, for from about 1 to 21 days.

5. The method of claim 4 wherein the bismuth is administered at a level of from about 50 milligrams to about 2500 milligrams, per day.

6. The method of claim 4 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

* * * * *